United States Patent [19]

Henkin

[11] 4,086,923
[45] May 2, 1978

[54] ALTITUDE CONDITIONING METHOD AND APPARATUS

[76] Inventor: Melvyn Lane Henkin, 19640 Greenbriar, Tarzana, Calif. 91356

[21] Appl. No.: 646,424

[22] Filed: Jan. 5, 1976

[51] Int. Cl.² ............................................. A61M 16/00
[52] U.S. Cl. .................................. 128/140 R; 128/202; 128/210; 128/147
[58] Field of Search .............. 128/185, 205, 204, 208, 128/209, 210, 211, 145 R, 2.08, 2 C, 2.07, 202, 203, 184, 142 R, 145.6, 147, 185, 191 R, 201, 142.2, 145 A

[56] References Cited

U.S. PATENT DOCUMENTS

| 2,227,536 | 1/1941 | D'Agostino | 128/192 |
| 2,844,145 | 7/1958 | Berge | 128/147 |
| 3,513,843 | 5/1970 | Exler | 128/202 |

FOREIGN PATENT DOCUMENTS

| 1,021,191 | 2/1953 | France | 128/2.08 |

Primary Examiner—Robert W. Michell
Assistant Examiner—Henry J. Recla
Attorney, Agent, or Firm—Lindenberg, Freilich, Hornbaker, Wasserman, Rosen & Fernandez

[57] ABSTRACT

A breathing method and apparatus for enabling a user, while at low altitude, e.g. sea level, to acclimate himself to high altitude conditions. The apparatus includes an inspiratory tube and an expiratory tube and means for selectively mixing a certain portion of oxygen depleted expired air with ambient air to supply air for inspiration. The first ends of the inspiratory and expiratory tubes are coupled to a mouth and/or nose breathing mask. The remote end of the expiratory path is coupled through a proportioning means to the environment and to a reservoir or air storage chamber. The remote end of the inspiratory path is also coupled to the proportioning means so as to pull ambient air from the environment, as well as oxygen depleted air from the reservoir. By varying the proportioning means, the ratio of ambient air to expired air, and thus the oxygen concentration of the inspired air, is varied so as to enable the user to select the particular elevated altitude to be simulated.

22 Claims, 10 Drawing Figures

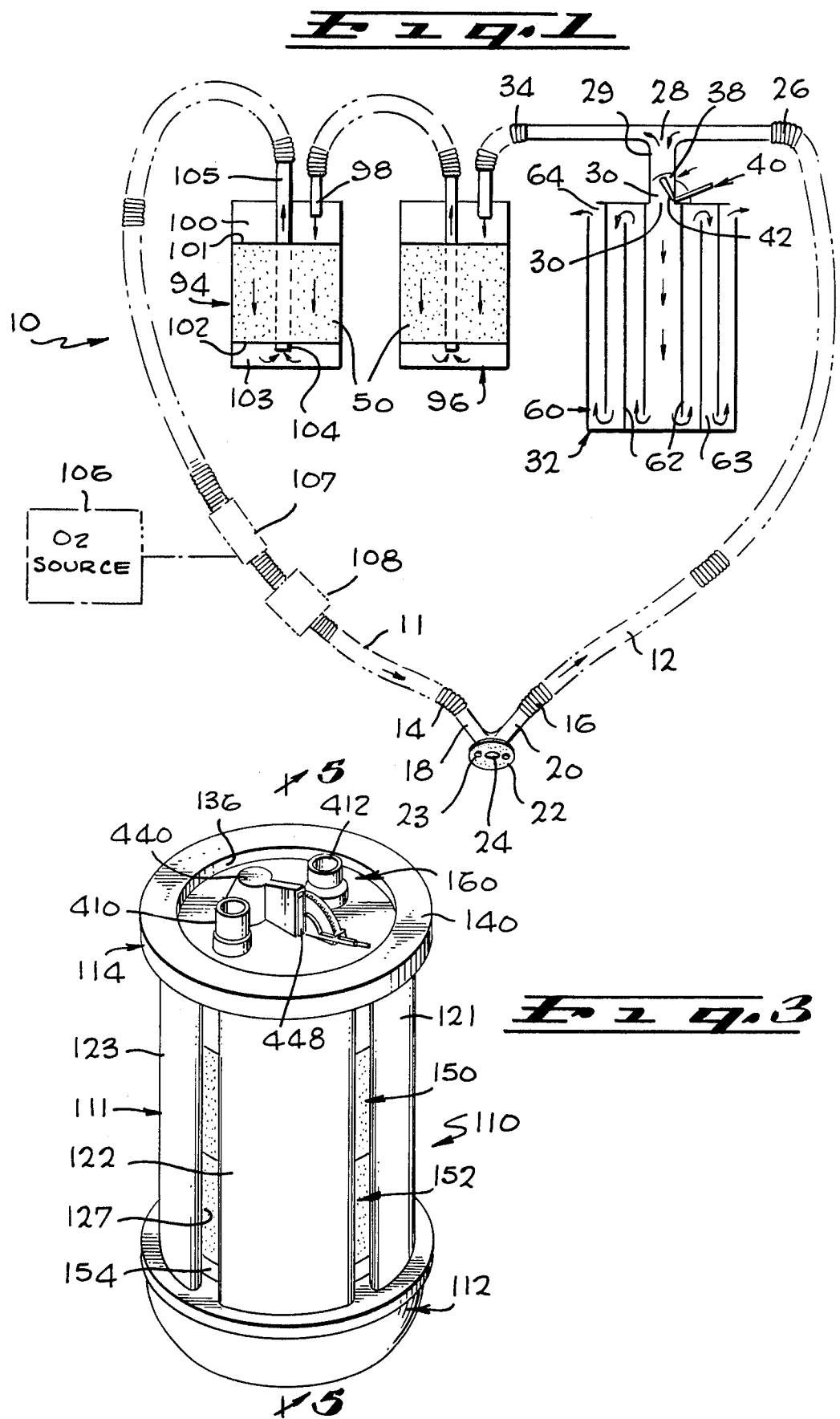

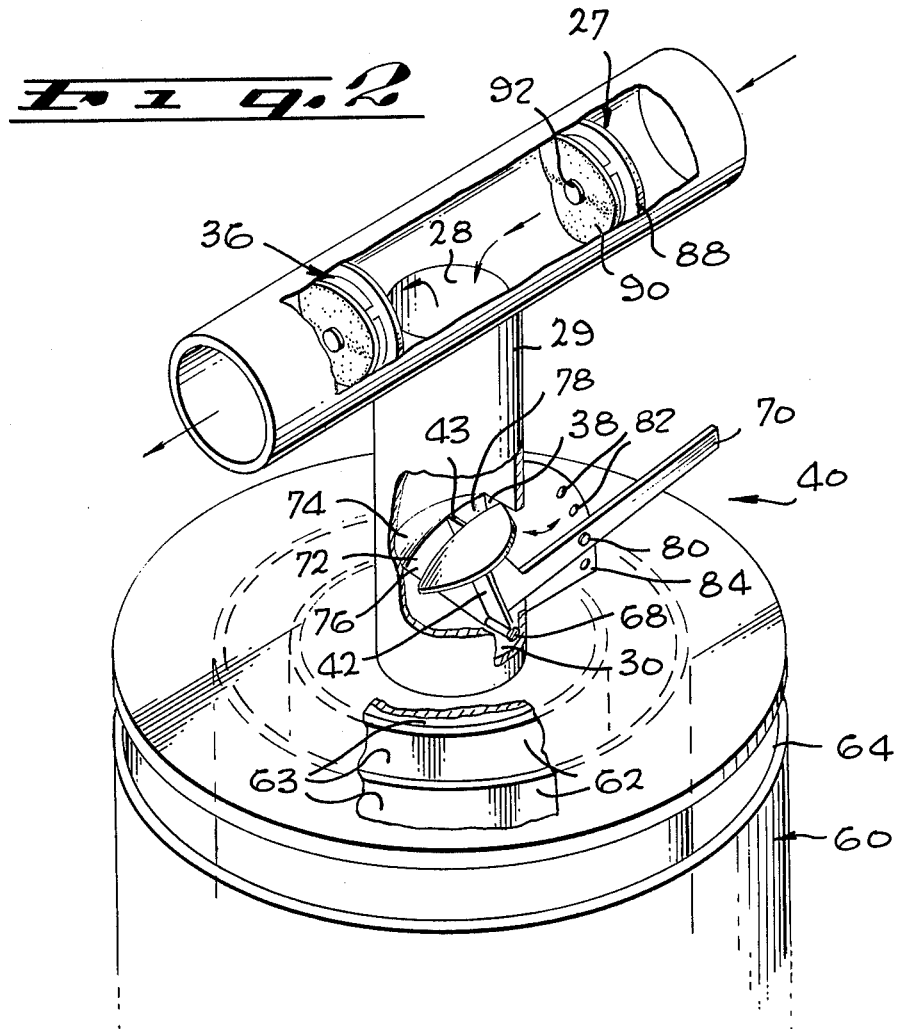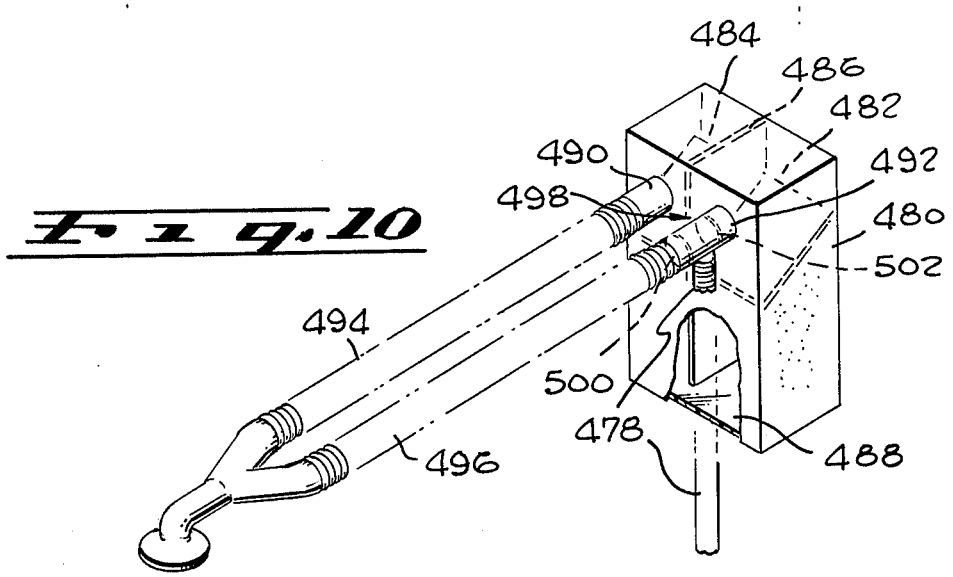

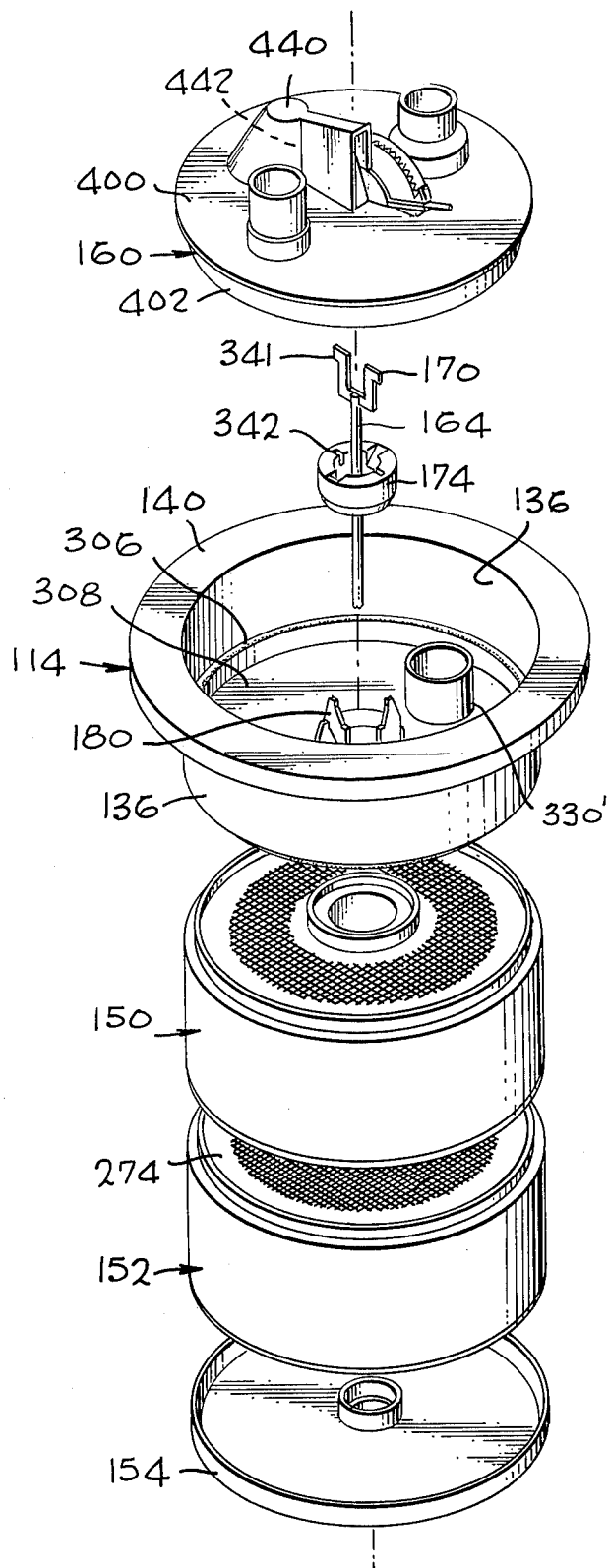
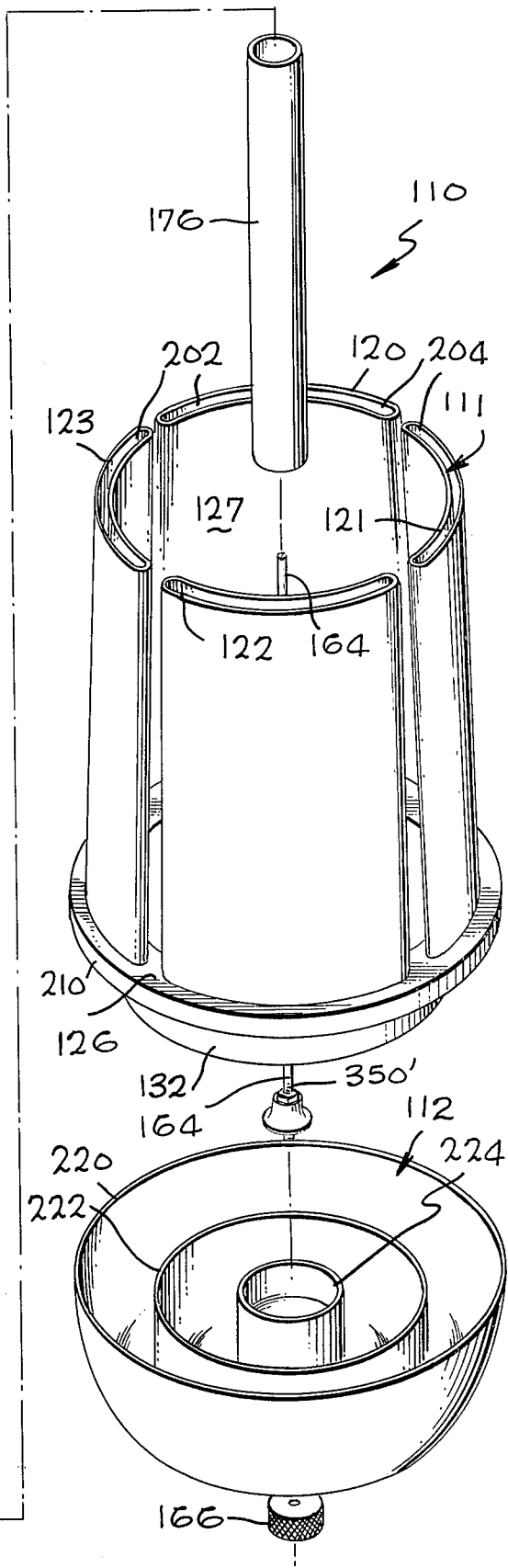
Fig. 4

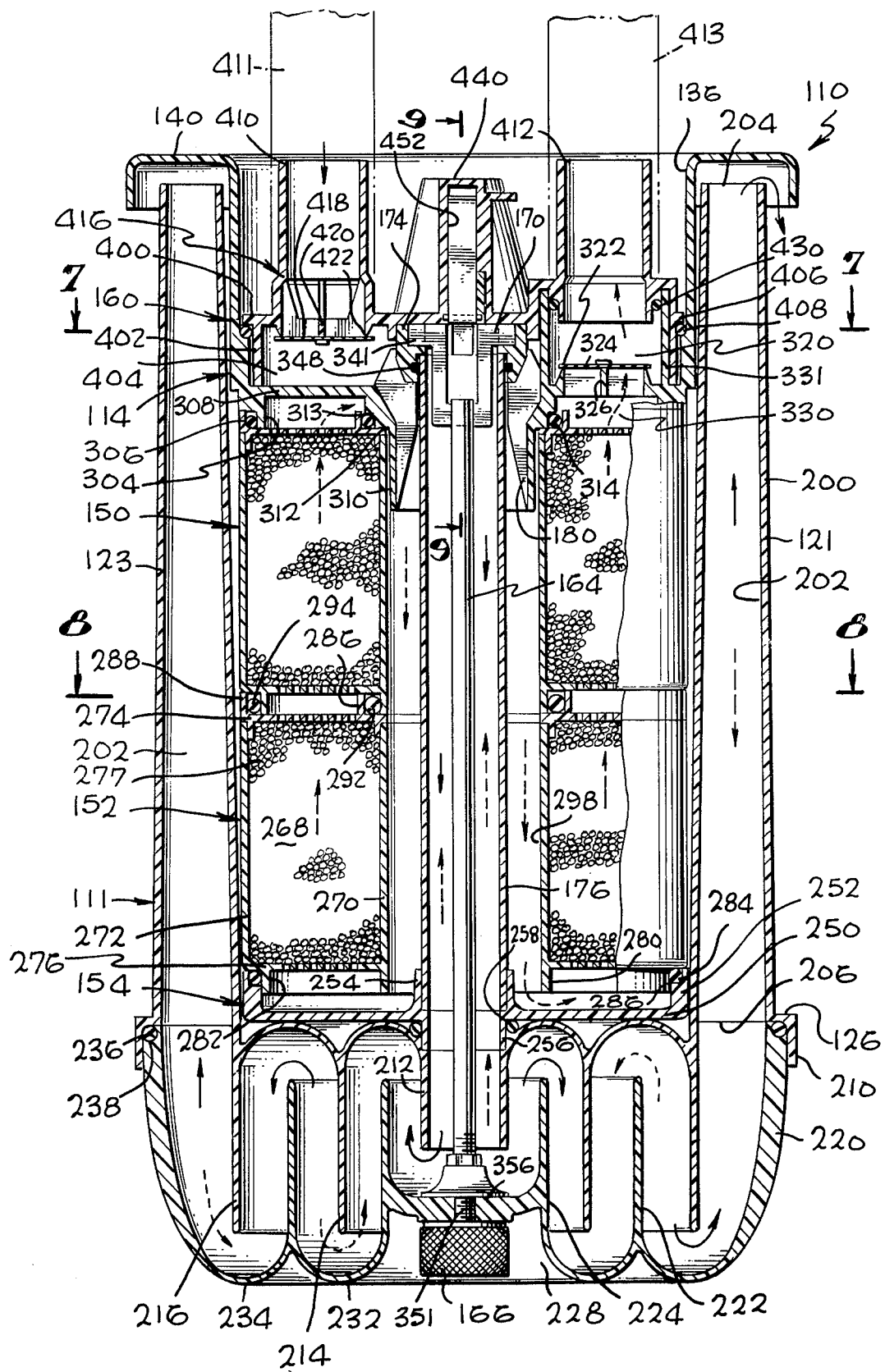

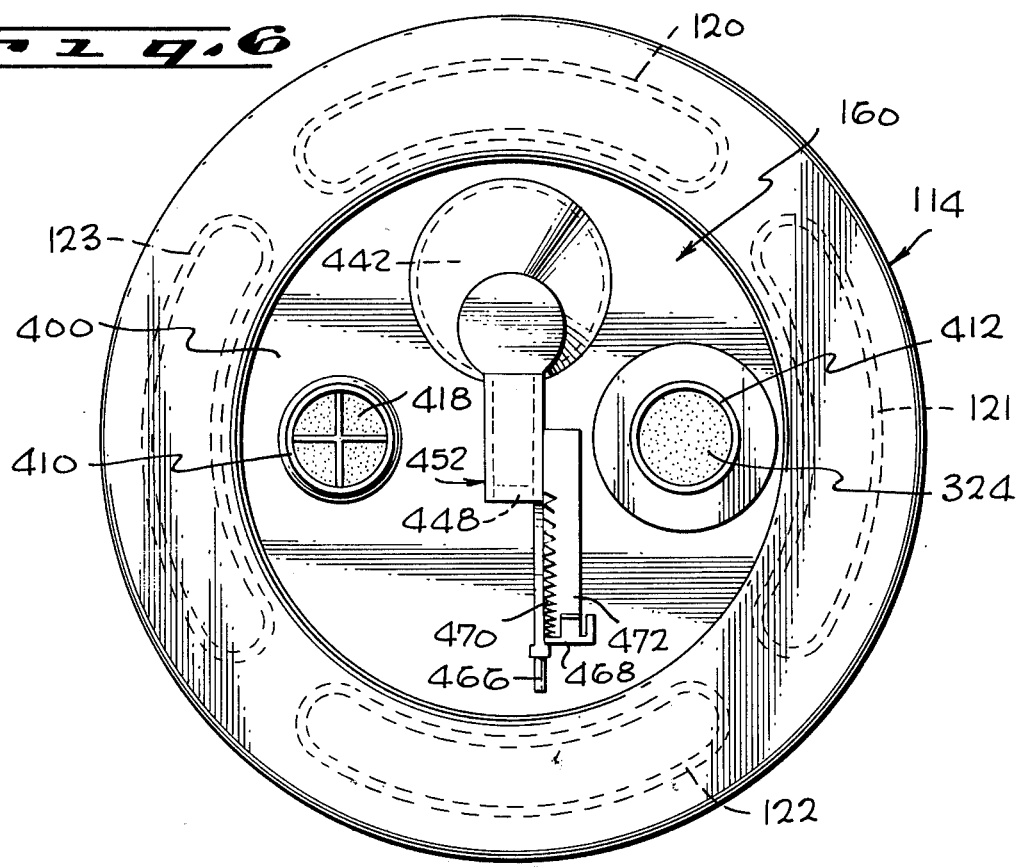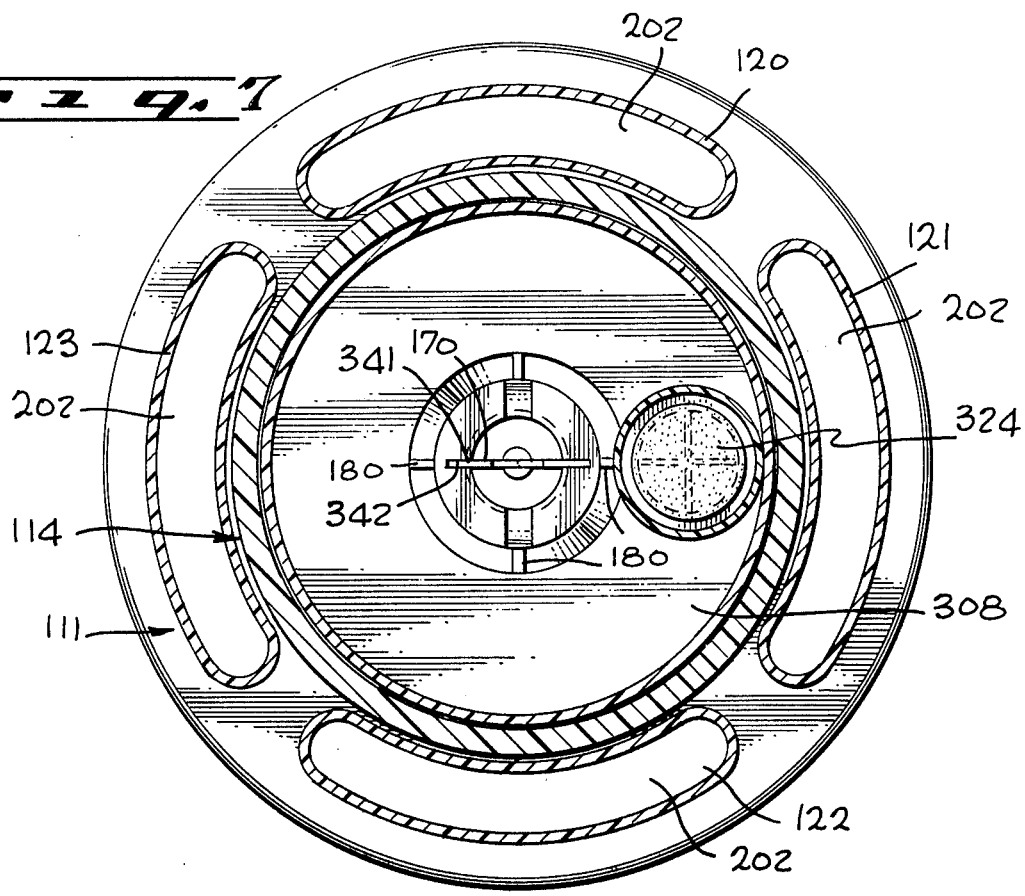

ALTITUDE CONDITIONING METHOD AND APPARATUS

BACKGROUND OF THE INVENTION

This invention relates generally to a breathing method and apparatus for supplying air to a user having a lower partial pressure of oxygen ($PO_2$) than the ambient air so as to simulate elevated altitude.

Persons who ordinarily function at a near-sea-level altitude frequently experience headache, shortness of breath, nausea, sleeplessness, and reduced endurance during the initial days at higher altitude, e.g. above 7,500 feet. These factors are, in large part, attributable to the diminishing amount of oxygen available as altitude increases. A typical situation involves a sea-level resident who occasionally takes a skiing weekend above 7,500 feet. As altitude increases, oxygen availability diminishes, thus requiring the person to breathe deeper in an effort to supply sufficient oxygen to his bloodstream. The partial pressure of oxygen ($PO_2$) at 7,500 feet is only 75% (of the $PO_2$ at sea level) and at 10,000 feet is only 65%. At 19,000 feet, the $PO_2$ is only 50%, thus meaning that a unit volume of air at 19,000 feet contains only half as much oxygen as that same unit volume at sea level. Typically, after a few days at the higher altitude, the person will become acclimated and the aforementioned problems subside. Interestingly, evidence suggests that persons who experience high altitudes on a frequent and regular basis appear to maintain a certain degree of acclimation to the altitude and are considerably better able to avoid the aforementioned problems than infrequent visitors.

SUMMARY OF THE INVENTION

The present invention is directed to a breathing method and apparatus for enabling a user, while at low altitudes, e.g. sea level, to acclimate himself to high altitude conditions.

In accordance with the invention, apparatus is provided for supplying air for inspiration by a user having a lower $PO_2$ than the ambient air. Partial pressure of oxygen ($PO_2$), as used herein, refers to the pressure attributable to the oxygen component in the air. The sum of the partial pressures of the various gas (air) components equals the total pressure at any altitude. Where $PO_2$ is expressed herein as a percentage, e.g. 50%, this percentage expresses the amount of oxygen present in a unit volume of air at a certain altitude as a percentage of the amount of oxygen in that same unit volume at sea level.

An apparatus in accordance with the invention preferably includes an inspiratory tube and an expiratory tube and means for mixing a certain portion of oxygen depleted expired air with ambient air to supply air for inspiration.

In accordance with a preferred embodiment of the invention, first ends of the inspiratory and expiratory tubes are coupled to a mouth and/or nose breathing mask. The remote end of the expiratory path is coupled through a proportioning means to the environment and to a reservoir or air storage chamber. The remote end of the inspiratory path is also coupled to the proportioning means so as to pull ambient air from the environment, as well as oxygen depleted air from the reservoir. By varying the proportioning means, the ratio of ambient air to expired air, and thus the oxygen concentration of the inspired air, is varied so as to enable the user to select the particular elevated altitude to be simulated.

In accordance with an important feature of the invention, in order to accommodate users having different tidal volumes and rates, a large capacity reservoir sufficient to accommodate the largest tidal volume user is provided. In accordance with a further feature, the reservoir is designed to assure smooth air flow with only negligible pressure drops.

In accordance with a further feature of the invention, carbon dioxide ($CO_2$) absorber material is incorporated in the system to remove the $CO_2$ from the expired air being rebreathed.

It is contemplated that a user will breathe through an apparatus in accordance with the invention for approximately 30-60 minutes per day, gradually increasing the elevation of the simulated altitude in increments of 2,000 to 3,000 feet, as he becomes acclimated to each altitude. Evidence of acclimation is indicated by only a small increase in pulse rate measured while performing mild exercise.

In addition to enabling a user to become acclimated to higher altitudes for the reasons aforestated, the method and apparatus in accordance with the invention is also useful for other purposes such as to increase endurance of competing athletes. That is, endurance during competition while breathing a certain $PO_2$ will be enhanced by training while breathing a lower $PO_2$.

Moreover, the physiology literature supports the inference that acclimation to elevated altitudes produces physiological changes in blood flow patterns, $O_2$ transport mechanisms and metabolic pathways which result in a marked reduction in the severity and incidence of cardiovascular problems. Accordingly, it is believed that altitude conditioning may be effective both to prevent and to treat cardiovascular problems.

BRIEF DESCRIPTION OF THE FIGURES

FIG. 1 is a schematic diagram of a breathing apparatus in accordance with the present invention showing the direction of air flow through the inspiratory and expiratory tubes and reservoir means;

FIG. 2 is an enlarged perspective view partially broken away showing the structure of the exemplary reservoir dipicted in FIG. 1;

FIG. 3 is a perspective view illustrating a preferred structural embodiment of the present invention;

FIG. 4 is a perspective exploded view of the embodiment of the invention illustrated in FIG. 3;

FIG. 5 is a vertical sectional view taken substantially along the plane 5—5 of FIG. 3;

FIG. 6 is a top plan view of the apparatus of FIG. 3;

FIGS. 7 and 8 are horizontal sectional views respectively taken along the planes 7—7 and 8—8 of FIG. 5;

FIG. 10 is a schematic perspective view of an alternate embodiment of the invention.

DESCRIPTION OF THE PREFERRED EMBODIMENTS

Figure 8:
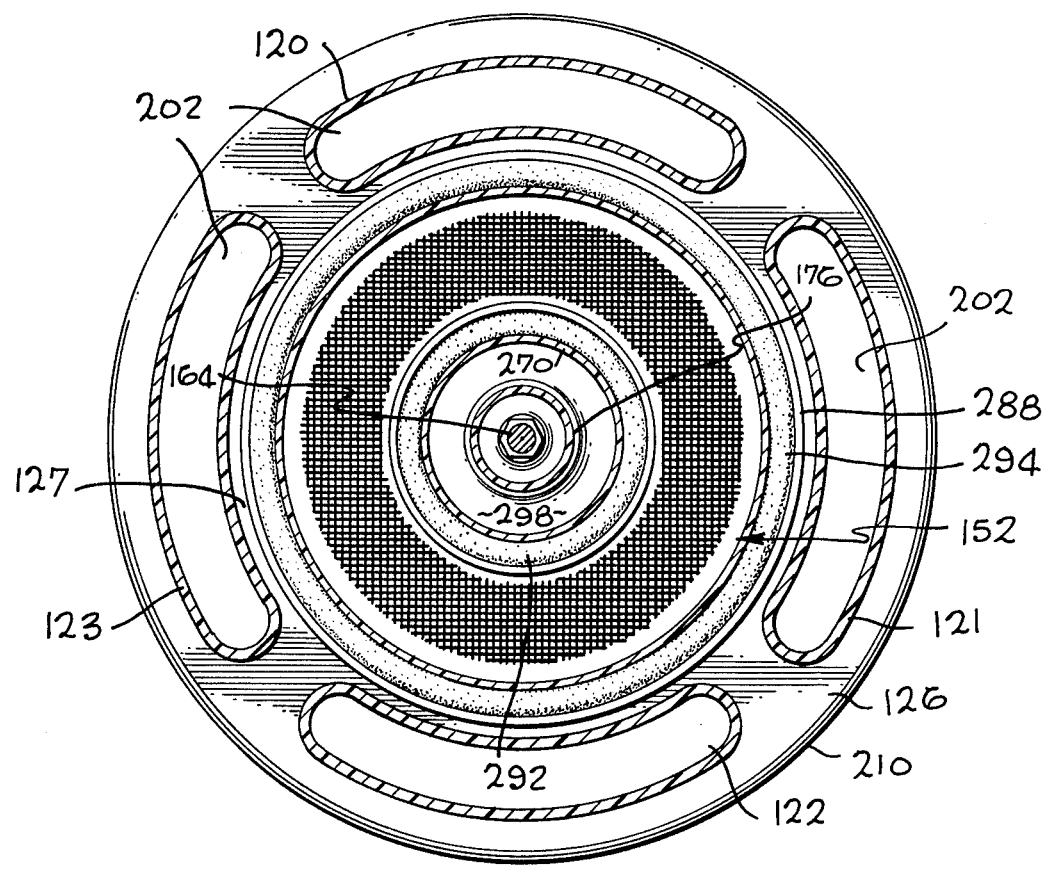

Attention is now directed to FIG. 1 which schematically illustrates a breathing apparatus 10 in accordance with the present invention for conditioning a user to the low oxygen conditions found at high altitudes. The user is able to condition himself to the low oxygen at high altitudes by breathing through the apparatus depicted in FIG. 1 for limited intervals for each day over an extended period of time. The apparatus of FIG. 1 supplies air for inspiration by the user whose oxygen content can be selectively varied to simulate virtually any altitude above ambient up to a physiologically safe level.

Briefly, apparatus in accordance with the invention functions to store expired, oxygen depleted air, in a reservoir and to mix this oxygen depleted air with ambient air to supply air for inspiration. By varying the proportion of ambient air mixed with oxygen depleted air from the reservoir, the oxygen concentration of the inspired air, and thus the altitude simulated, can be varied.

The exemplary system 10 in FIG. 1 is comprised of an inspiratory tube 11 and an expiratory tube 12 (preferably formed of conventional corrugated tubing similar to that used in anesthesia delivery systems) each having their first ends, 14 and 16 respectively, coupled to nipples 18 and 20 of a patient mouth piece 22, illustrated as including a port 24 for communicating with a user's air channel through his mouth. However, it should be understood that a nose or full face mask can be utilized in the alternative.

The expiratory tube 12 terminates at a second end 26 and includes a one-way expiratory valve 27 (FIG. 2) mounted therein for restricting air flow from the first end 16 to the second end 26 of the tube 12. The second end 26 of the expiratory tube 12 opens into entrance opening 28 of pipe section 29. Pipe section 29 includes a second opening 30 which communicates with the entrance opening 31 of a reservoir or air storage chamber 32. The entrance opening 28 of pipe section 29 also communicates with a second end 34 or the inspiratory tube 11. A one-way check valve 36 (FIG. 2) is incorporated in the inspiratory tube 11 for restricting air flow therein from the second end 34 to the first end 14 of the tube 11.

The pipe section 29, in addition to opening into the reservoir 32, opens to the environment through port 38. A proportioning valve mechanism 40 is mounted in the pipe section 29 and includes a baffle 42 for varying the air flow path dimensions between the paths from pipe section entrance opening 28 to the environment through the port 38 and to the reservoir 32 through opening 30. That is, in a first extreme position of the proportioning valve mechanism 40, the pipe section entrance opening 28 communicates primarily with the ambient air environment through port 38, and in the opposite extreme position, communicates primarily through the opening 30 to the reservoir 32.

Carbon dioxide ($CO_2$) absorber material 50 is incorporated in the inspiratory tube 11 for removing carbon dioxide from the air flowing from the second end 36 to the first end 14 of inspiratory tube 11.

In the use of the apparatus of FIG. 1, a user would grip the studs 23 of mouth piece 22 between his teeth so as to communicate the opening 24 with the user's air channel through his mouth. The user would then breathe through his mouth in normal fashion for a certain interval of time, e.g. 30–60 minutes. On each expiration, the expired air flows through the tube 12 from the first end 16 to the second end 26 thereof and into pipe section 29. A portion of the expired air will be exhausted through port 38 to the environment. The remaining portion of the expired air will enter the reservoir 32 through pipe section opening 30 and be stored therein. On inspiration, the user will pull air into the second end 34 of inspiratory tube 11 from the environment through port 38 and from the reservoir 32 through pipe section opening 30. The air pulled from the reservoir 32 will, of course, have a lower oxygen concentration than the ambient air pulled through port 38 from the environment. By varying the position of proportioning baffle 42, the oxygen concentration of the air to be inspired by the user can be caused to be either closer to that of the oxygen depleted expired air stored in reservoir 32 of the ambient air available through port 38. In any event, the air drawn into the inspiratory tube through the inspiratory check valve 36 is steered through the $CO_2$ absorber material 50 in order to remove therefrom the carbon dioxide contained in the expired air drawn from the reservoir 32. This air then flows through the inspiration tube 11 to the first end 14 and is inspired by the user.

Now considering the system of FIG. 1 in greater detail, it should be recognized that the total volume of air expired on each breath by a user is divided into two variable portions; the first portion exits through port 38 and dissipates in the environment and the second portion enters the reservoir 32. It is important that the reservoir 32 have a sufficient capacity to be able to supply enough oxygen depleted air during the inspiration phase to reduce the amount of oxygen in the inspired air to correspond to the maximum altitude it is desired to simulate. In accordance with the preferred embodiment of the invention, this maximum altitude is 19,000 feet at which the $PO_2$ is 50%. Moreover, the reservoir 32 must have the capacity to provide sufficient oxygen depleted air to simulate this altitude for the largest tidal volume user. Based on the foregoing, it has been determined that a reservoir capacity of about 4 liters is sufficient to accommodate virtually the largest tidal volume user to an altitude of approximately 19,000 feet.

On an inspiration phase of tidal volume equal to the tidal volume of the prior expiration, all of the expired gas stored in the reservoir 32 reverses direction and flows into the inspiratory tube 11. Additionally, a volume of ambient air equal to the volume of expired air expelled through the port 38 on expiration, is drawn into the inspiratory tube to be mixed with the expired air drawn from the reservoir 32 to create a total volume of air to be inspired equal to the volume previously expired. It is preferable that the reservoir 32 be designed so as to permit easy flow of the air into and out of it so as to avoid introducing any resistance to the user's breathing. In order to facilitate smooth non-turbulent air flow, the reservoir 32 can be constructed as is represented in FIGS. 1 and 2.

More particularly, the reservoir 32 is comprised of a cylindrical housing 60 containing a plurality of spaced vertical cylindrical baffles 62 concentrically arranged to define a central cylindrical volume surrounded by toroidal volumes 63 of increasing radius. The baffles are dimensioned so as to define a series air flow path through the respective volumes. That is, as can be seen in FIGS. 1 and 2, the pipe section 29 opens into housing entrance opening 30 communicating with the aforementioned central volume. This central volume is defined by the smallest radius baffle 62 whose lower edge is spaced from the bottom of housing 60 so as to permit air flow to or from the immediately surrounding toroidal volume. Note that the space between the baffles 62 and housing 60 is alternated between the baffle lower and upper edges to thereby define a series air flow path extending from entrance opening 30 toward overflow opening 64. The housing is open to the environment at 64 to permit the air in the housing to be pushed out ahead of newly expired air entering the housing via entrance opening 30, thus avoiding the buildup of back pressure which would make breathing difficult.

In use, on each expiration, expired air is exhausted into the cylindrical housing 60 and stored within the series coupled volumes defined by baffles 62. On the subsequent inspiration, the stored air is retrieved flowing in a direction from the overflow opening 64 toward the entrance opening 30.

The proportioning valve mechanism 40, as is better shown in FIG. 2, is comprised of a baffle 42 mounted for pivotal movement about pin 68. Connected to the baffle 42 is a lever arm 70 for facilitating movement of the baffle about the pivot pin 68. The end 43 of the baffle 42 moves in a slot 72 formed in a wall 74 conforming to and closing the interior of pipe section 29. The end 43 of baffle 42 divides the slot 72 into a first section 76 communicating the pipe section opening 28 with the opening 30 to the reservoir 32 and a second section 78 which communicates the pipe section opening 28 with the port 38 to the environment. The lever arm 70 carries a detent 80 selectively engageable with any one of a plurality of holes 82 formed in a plate 84 fixedly mounted on the top of cylindrical housing 60. Thus, by engaging the detent 80 on lever arm 70 with one of the holes 82, the ratio between the areas of sections 76 and 78 of the slot 72 can be varied so as to in turn vary the ratio of air flow between the reservoir and the environment. The range of movement of the baffle 42 is limited so as to prevent complete closure of the flow path to the environment. That is, when used close to sea level, the extreme closed position of baffle 42 still assures sufficient air flow to and from the environment via section 78 to limit the altitude simulated to 19,000 feet. FIG. 2 also illustrates the expiratory check valve 27 in greater detail and it can be seen to comprise an apertured valve seat frame 88 and a flexible valve disk 90 retained at its center 92. The disk 90 is mounted on the downstream side of the valve seat frame 88 so as to permit air flow past the valve seat frame and around the disk 90. Air flow in the opposite direction is prevented since such flow would merely seat the valve disk 90 against the valve seat frame 88. The inspiratory valve 36 can be constructed identically to the expiratory valve 27.

FIG. 1 illustrates the utilization of two separate cannisters 94 and 96 of $CO_2$ absorber material 50. Each cannister includes an air entrance opening 98 which communicates with an upper air chamber 100. The $CO_2$ absorber material 50 is retained between an upper apertured plate 101 and a lower apertured plate 102. Air flow is from the upper chamber 100 through the upper plate 101, through the $CO_2$ absorber material 50, and through the lower plate 102 to a lower air chamber 103. The air then flows through the chamber 103 through a central pipe section 104 to the air exit opening 105.

FIG. 1 further illustrates (by dashed line) devices which may be optionally incorporated in the system thus far explained to make it more suitable for particular applications. For example only, it has now been recognized that apparatus in accordance with the present invention may prove quite useful for evaluating pathologic cardiac deficiencies by subjecting a user to an oxygen reduced concentration or simulated high altitude, and monitoring his vital signs and EKG. Where the apparatus is used in such an application, it is desirable to provide means for rapidly administering supplemental oxygen into the inspiratory tube 11 in the event the user experiences difficulties at the altitude setting of the device. Accordingly, FIG. 1 illustrates an oxygen source 106 coupled by a valve mechanism 107 to the inspiratory tube 11. It is contemplated, of course, that apparatus of the type shown in FIG. 1 for the aforementioned application to evaluate pathologic cardiac conditions, would be used only under the care of an attending physician.

As a still further variation, it may be desirable to incorporate an oxygen sensing meter 108 in the inspiratory tube 11 to accurately measure inspired oxygen concentrations. It is not contemplated that such a measurement be desirable in typical applications of the present invention but, indeed, it may be desirable in certain situations to enable the verification of the simulated altitude.

Attention is now directed to FIGS. 3–9 which illustrate a preferred structural embodiment of the invention. FIG. 3 illustrates a perspective view of an air storage and valve assembly 110 which need only be connected to inspiratory and expiratory tubes and a breathing mask to form a complete system in accordance with the present invention, as depicted in FIG. 1. In order to facilitate an understanding of the structure and functioning of the air storage and valve assembly 110, attention is initially directed to the exploded view of the assembly illustrated in FIG. 4.

The outer structure of assembly 110 is basically formed by an air storage chamber columnar section 111, an air storage chamber bowl section 112, and an inspiratory valve subassembly 114. Briefly, the air storage chamber columnar section 111 is comprised of four hollow columnar members 120, 121, 122 and 123 which extend vertically from a base plate 126. The columnar members 120, 121, 122, and 123 are each arcuately shaped and spaced from one another along the circumference of a circle formed on base plate 126 to form a substantially cylindrical wall enveloping a central volume 127. The columnar members are each open at their top and bottom. Depending from the undersurface of the base plate 126 are concentric walls 132 oriented to cooperate with concentric walls of the air storage chamber bowl section 112, as will be described hereinafter.

The inspiratory valve subassembly 114 includes a cylindrical wall 136 adapted to fit within the cylindrical central volume 127 defined by columnar members 120, 121, 122 and 123 of the air storage chamber columnar section 111. The inspiratory valve subassembly 114 additionally includes a lip 140 which extends radially outwardly from the upper end of wall 136 and which, when assembled, hangs over, but is spaced from, the open upper ends of columnar members 120, 121, 122 and 123.

Still referring to FIG. 4, first and second $CO_2$ cannisters 150 and 152 are provided to be received in stacked relationship within the cylindrical central volume 127 defined by the columnar members 120, 121, 122 and 123 immediately above a collection tray 154. An expiratory and proportioning valve subassembly 160 is provided to be received over the inspiratory valve subassembly 114 within the cylindrical cavity defined by wall 136.

The subassembly elements thus far discussed including the inspiratory valve subassembly 114, the $CO_2$ cannisters 150 and 152, the tray 154, the base plate 126 of the air storage chamber columnar section 111 and the air storage chamber bowl section 112 are all provided with central openings through which a tie rod 164 is passed. The lower end of the tie rod is threaded for receiving a knurled nut 166 beneath the bowl section 112. The upper end of the tie rod 164 terminates in a horseshoe bracket 170 engageable in a retaining ring 174. The retaining ring 174 engages and bears against fins 180 extending radially inwardly within the central opening of the inspiratory valve subassembly 114. Thus, by threading the knurled nut 166 onto the threaded lower end of the tie rod 164, the inspiratory valve subassembly 114, air storage chamber columnar section 123 and air storage chamber bowl section 112 can be pulled together with the $CO_2$ cannisters 150 and 152 retained therein. The assembly 110 additionally includes an open rigid tube section 176 which fits around the tie rod 164 between the retaining ring 174 and tray 154.

Attention is now directed to FIGS. 5-9 which illustrate in greater detail the structure of the air storage and valve assembly 110 depicted in FIGS. 3 and 4. As noted, the assembly 110 includes as a major subassembly, the air storage chamber columnar section 111 formed by four upstanding columnar members 120, 121, 122 and 123. Each of these columnar members is formed by a vertical wall 200 defining a closed path enveloping a columnar volume 202. The volume 202 opens at 204 adjacent the upper end of the wall 200 (as seen in FIG. 5) and at 206 adjacent the lower end of the wall. The columnar members 120, 121, 122 and 123 extend upwardly from a base plate 126 having an enlarged diameter depending cylindrical flange 210. Depending from the underside of base plate 126 of the air storage chamber columnar section 111 are downwardly projecting concentric annular walls 212, 214, and 216. The columnar volumes 202 defined by the columnar members 120, 121, 122 and 123 open at their lower end 206 radially outwardly from depending concentric wall 216.

Air storage chamber bowl section 112 is comprised of outer cylindrical wall 220 and concentric upwardly projecting cylindrical walls 222 and 224. The undersurface of bowl section 112 is recessed at 228 to enable the previously mentioned knurled nut 166 to be received therein. This assures that the assembly 110 can rest and be stable on a horizontal table surface (not shown) resting on the undersurface of bowl section 112 along concentric annular surfaces 232 and 234. The upper outer edge of bowl section wall 220 is recessed at 236 for receiving an O-ring 238 to provide an air seal between wall 220 and depending lip 210 of the air storage chamber columnar section 111. As can be clearly seen in FIG. 5, when the air storage chamber sections 111 and 112 are assembled together, the depending concentric walls 214 and 216 of the section 111 are interleaved with the upwardly extending concentric walls 220, 222, and 224 of the bowl section 112. For purposes to be described hereinafter, the interleaving of the walls of sections 111 and 112 provide an air flow path from the cylindrical volume enveloped by inner wall 212 of section 111 to the interstice between wall 212 and wall 224 of bowl section 112 to the interstice between wall 224 and wall 214 of section 111, to the interstice between wall 214 and 222 of bowl section 112, to the interstice between wall 222 and wall 216 of section 111, and then through the interstice between wall 216 and bowl section outer wall 220 to the columnar volumes 202 defined by the columnar members 120, 121, 122 and 123.

As seen in FIG. 5, the condensation tray 154 is disposed immediately above and rests on the base plate 126 of the air storage chamber columnar section 111. The tray 154 includes a floor 250, an upwardly extending outer wall 252, and an upwardly extending inner wall 254 surrounding a central opening for receiving the lower end of rigid open tube 176. Tray 154 also includes a downwardly depending cylindrical wall 256 which projects into the cylindrical volume defined by depending wall 212 of air storage chamber columnar section 111. O-ring 258 prevents air leakage along the boundary between tray wall 256 and the base plate 126.

The lower $CO_2$ cannister 152 is supported on the upper surface of wall 252 of tray 154. The cannister 152 is comprised of a toroidal container including an inner cylindrical wall 270 and an outer cylindrical wall 272. The toroidal volume 268 defined between the walls 270 and 272 is enclosed on the top by a perforated plate 274 and on the bottom by perforated plate 276. The toroidal volume 268 is filled with $CO_2$ absorber material 277 having a granule size larger than the perforations in the upper and lower plates 274 and 276. Extending downwardly from the lower perforated plate 276 of cannister 152 are concentric flanges 280 and 282. Flange 282 cooperates with O-ring 284 received in an upper recess 286 of tray wall 252 to form an air seal between flange 282 and wall 252.

Extending upwardly from the top perforated plate 274 are a pair of concentric flanges 286 and 288. The flanges 286 and 288 cooperate with depending flanges on the upper cannister 150 to retain O-rings 292 and 294. It is pointed out that the cannisters 150 and 152 are identically constructed and dimensioned so that they are completely interchangeable. It is to be noted that the inner cylindrical wall 270 of each of the cannisters 150 and 152 is dimensioned so as to be spaced outwardly from the rigid tube 176 so as to define a toroidal air passage 298 extending vertically and opening at its lower end into tray 154 around flange 280.

The inspiratory valve subassembly 114 includes a cylindrical vertical wall 136 dimensioned to fit downwardly into the cylindrical central volume 127 defined by the columnar members 120, 121, 122 and 123. When fitted in this cylindrical central volume, the outer suurface of wall 136 engages the inner annular surface of the columnar members with the radially outwardly extending lip 140 of subassembly 114 centilevered out over the open ends 204 of the columnar members 120, 121, 122 and 123. As can be noted in FIG. 5, clearance is provided between the upper ends of wall 200 and the lip 140 so as to permit unrestricted air flow therebetween.

The subassembly 114 includes a downwardly extending cylindrical flange 304 dimensioned to fit within the outer cylindrical flange extending upwardly from the upper perforated plate of cannister 150 to receive O-ring 306 therebetween. The subassembly 114 further includes a horizontal floor 308 formed above the lower edge of flange 304. A central opening is formed in the floor 308 with a cylindrical wall 310 depending from the floor 308 around the central opening. A shoulder 312 is formed on the outer surface of wall 310 which rests on the upper perforated plate of cannister 150. Additionally, a recess 313 is formed in wall 310 to position an O-ring 314 adjacent the inner upwardly extending flange from the upper perforated plate of cannister 150. The wall 310 depending from floor 308 is dimensioned so as to fit within the inner cylindrical wall of the cannister 150.

Also formed within the floor 308 of subassembly 114 is an opening 320. An upwardly projecting knife edge 322 is defined around the opening 320 to constitute a valve seat against which a flexible valve disc element 324, centrally retained by pin 326, can seat to prevent downward (as viewed in FIG. 5) airflow therepast. The undersurface of the floor 308 forms a toroidal chamber 330 above the upper perforated plate of cannister 150 from which air is able to flow past the valve element 324 in an upward direction only. Extending upwardly from the upper side of floor 308 is a cylindrical wall 331 surrounding the knife edge 322.

Extending radially inwardly from the inner surface of depending cylindrical wall 310 of subassembly 114 are a plurality of radial fins 340. The fins are circumferentially spaced from one another around tube 176 to permit airflow therebetween from above the upper surface of floor 308 into the toroidal volume 298. The inner edges of fins 340 are dimensioned so as to closely receive the tube 176. The upper edges of fins 340 are shaped to define a seat for retaining ring 174. Retaining ring 174 defines a central opening through which the horseshoe shaped bracket 170 depends. Outwardly projecting ears 341 fit into radially projecting slots 342 formed in the ring 174. The lower horizontal edges of ears 341 on bracket 170 bear against the floor of slot 342 so that a downward pull, as depicted in FIG. 5, on the bracket 170, pulls the retaining ring 174 downward against the fins 340. The central opening in the ring 174 is dimensioned so as to fit the upper end of tube 176 therein. A recess 348 is provided for receiving O-ring 350 around the upper end of tube 176.

From what has been said thus far with respect to the elements in FIG. 5, it should be apparent that the subassembly 114, cannisters 150 and 152, tray 154, and air storage chamber sections 110 and 112, can be assembled by threading the knurled nut 166 onto the lower threaded end 351 of the tie rod 164. As the nut 166 is threaded onto the tie rod 164, the bowl section 112 is moved upwardly against a fixed shoulder 356 carried by the tie rod to seat the bowl section wall 220 and O-ring 238 within the depending lip 210 of columnar section 111. Additionally, as the knurled nut is being treated, the horseshoe bracket 170 is being pulled downwardly to in turn cause the retaining ring 174 to be pulled downwardly against the fins 340.

As previously pointed out, the expiratory and proportioning valve subassembly 160 is received within the central cylindrical cavity defined by the wall 136 of the inspiratory valve subassembly 114. The expiratory and proportioning valve subassembly 160 is essentially comprised of a circular base plate 400 having a cylindrical flange 402 depending therefrom. The flange 402 rests on the floor 308 of subassembly 114 so as to space the base plate 400 of subassembly 160 above the floor 308 of subassembly 114 to thereby define a pathway or chamber 404 therebetween. The base plate 400 extends radially beyond the flange 402 at 406 and a sealing O-ring 408 is received between the outer surface of flange 402 and the inner surface of wall 136 of subassembly 114.

Extending upwardly from the base plate 400 of subassembly 160 is an expiratory nipple 410 and an inspiratory nipple 412. As shown in dashed lines, the expiratory tube 411 is received over and communicates with the interior of the expiratory nipple 410. Similarly, the inspiratory tube 413 is received over and communicates with the interior of inspiratory nipple 412. An expiratory check valve 416 comprised of valve element 418 anchored by center pin 420 is retained immediately below the expiratory nipple 410. A knife edge valve seat 422 is formed around the terminal edge of the volume enclosed by nipple 410. Configured as shown, the expiratory valve element 418 will permit air flow from the expiratory tube 104 downwardly past the valve element 418 into the chamber 404. Air flow in the opposite direction is, of course, prevented.

The inspiratory nipple 412 opens at its lower end into the chamber 404 immediately above valve element 324 of the inspiratory valve. It will be recalled that the valve element 324 will permit air flow from compartment 330 into the chamber 404 for flow into the inspiratory tube 102 but will not permit air flow in the opposite direction from the chamber 404 to the compartment 330. It will be noted that the inspiratory nipple 412 extends down into the wall 331 of the subassembly 114 with an O-ring 430 being provided for sealing.

Figure 9:
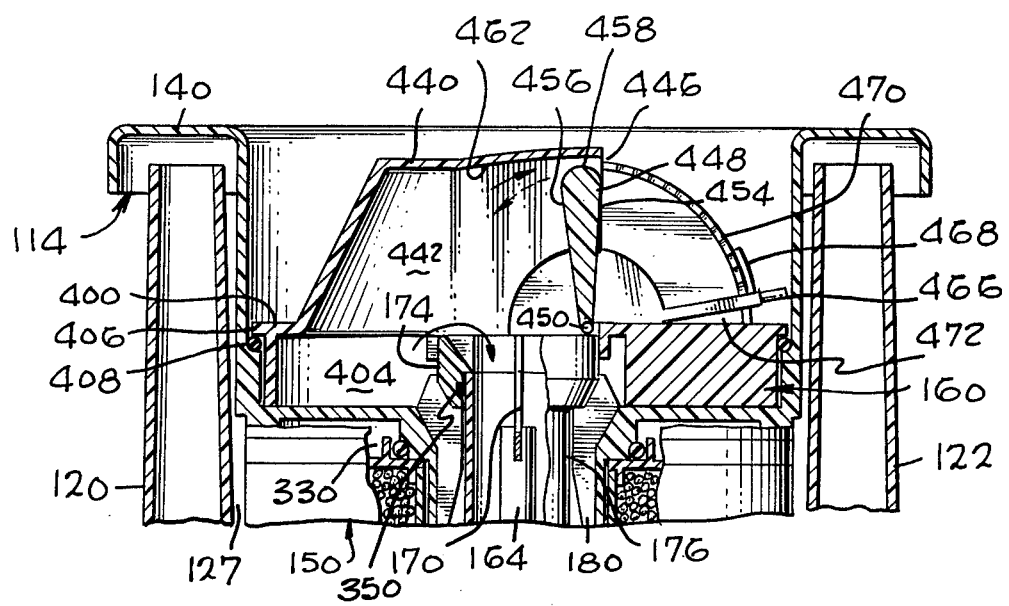
FIG. 9 is a vertical sectional view taken substantially along the plane 9—9 of FIG. 5.

The expiratory and proportioning valve subassembly 160 is shaped (as is best shown in FIGS. 5 and 9) to form a protuberance 440 rising upwardly from the base plate 400. Internally, the base plate envelopes a proportioning valve chamber 442 which communicates with the environment 446 (beyond proportioning valve element 448) and with the chamber 404.

The proportioning valve element 448 is mounted for pivotal movement about pin 450. The element 448 is substantially flat and has a width approximately equal that of slot 452 (FIG. 5) comprising the entranceway from the environment 446 into the proportioning valve chamber 442. The valve element 448 is designed with slightly diverging front and rear walls 454 and 456 and with a smoothly curved end surface 458 to assure smooth non-turbulent air flow therepast. As shown in FIG. 9, when the valve element 448 is positioned vertically, it substantially closes the entrance slot 452 and thereby substantially cuts off communication between the environment and the proportioning valve chamber 442. As will be discussed hereinafter, the assembly is preferably designed such that the extreme position of the valve element 448 (depicted in FIG. 9) never entirely seals the entrance slot 452 but rather always assures at least a certain ambient air flow into the proportioning valve 442. The radial distance from the pin 450 to the edge surface 458 of proportioning valve 448 differs from that of the interior surface 462 of protuberance 440. That is, the radius of the interior surface 462 is shaped such that as the valve element 448 is pivoted from the position depicted in FIG. 9 in a counter-clockwise direction, the distance between the valve element edge surface 458 and the interior surface 462 increases. As a consequence, by pivoting the valve element 448 in a counter-clockwise direction, the passageway area communicating the environment 446 with the proportioning valve chamber 442 is increased to thereby permit a corresponding increase in ambient air flow into and out of the chamber 442.

The position of the valve 448 is controlled by a manually movable lever 466. Lever 466 carries a detent means 468 which cooperates with notches 470 formed in a fixed plate 472 mounted on the base plate 400 of subassembly 160. Thus, the particular pivotal position of the valve element 448 relative to the protuberance inner surface 462 can be established by the user by selectively detenting the lever detent means 468 in a selected slot 470.

As previously described, in utilizing the apparatus of FIGS. 3–9, a user will merely breathe through the breathing mask (FIG. 1) and adjust the position of valve element 448 (FIG. 9) to establish the altitude desired to be simulated. The highest simulated altitude is achieved when the valve element 448 is in the full line position shown in FIG. 9 whereat only very little ambient air flows therepast into the proportioning valve chamber 442. The lowest simulated altitude is achieved by moving the valve element 448 to the extreme counter-clockwise position to provide maximum communication between the environment 446 and the chamber 442. In order to understand the functioning of the apparatus of FIGS. 3-9, the air flow path from the expiratory tube 411 into the assembly 110 will first be discussed in connection with FIGS. 5-9. Air flow during an expiration phase is represented by solid line arrows shown in FIGS. 5 and 9. Air flow during an inspiration phase is represented by dashed line arrows also shown in FIGS. 5 and 9.

During an expiration phase, the user will create a positive pressure in both expiratory tube 411 and inspiratory tube 413. This will open expiratory valve 416 permitting expired air to flow from tube 411 past valve element 418 into chamber 404. This expired air is, of course, oxygen depleted and generally contains approximately 5% less oxygen than the air previously inspired. The expired air entering the chamber 404 will split into essentially two paths; (1) a certain portion of the expired air will move from the chamber 404 through the proportioning chamber 442 and out past the valve element 448 to the environment 446, and (2) a certain portion of the expired air will move from the chamber 404 into the proportioning chamber 442 and then down through the retaining ring 174 into the tube 176.

The proportioning between the two aforementioned components of expired air depends upon the position of the proportioning valve 448. That is, more expired air will be lost to the environment as the valve element 448 is moved counter-clockwise to increasingly open the entrance slot 452. The component of expired air entering the interior of tube 176 will pass down the tube and thence along the undulating air channel between walls 212, 224, 214, 222, 216 and into the columnar volumes 202. If the volume of expired air component following this path exceeds the capacity of the columnar volumes, it will merely overflow out the top of the columnar volumes at 204.

During the succeeding inspiration phase, a negative pressure will be produced in expiratory tube 411 and inspiratory tube 413 and as a consequence will seal valve element 418 and open valve element 324 to permit air to be drawn into the inspiratory tube 413. As previously discussed in connection with FIG. 1, the air drawn into the inspiratory tube 413 will be comprised of ambient air drawn from the environment and expired oxygen depleted air stored within the assembly 110. More particularly, the negative pressure created by the user in inspiratory tube 413 will draw a component of air from the environment 446 past the proportioning valve element 448 into the chamber 442 and then to the passageway 404. Passageway 404 of course opens into toroidal volume 298. Thus, for a particular negative pressure, it will be recognized that the position of the proportioning valve element 448 determines the amount of ambient air drawn into the toroidal pathway 298.

The other component of inspired air is drawn upwardly through the tube 176 from the columnary volumes 202 and the path defined by walls 216, 222, 214, 224 and 212. This air from tube 176 passes through retaining ring 174 into the proportioning chamber 442. Thus, both the ambient air and stored expired air components are mixed in the chamber 442. This mixture then flows from the chamber 442 past the fins 340 into the toroidal volume 298 around tube 176 down to the tray 154. This air is then drawn upwardly through the $CO_2$ absorber material 268 within cannisters 150 and 152 and into the chamber 330. From the chamber 330, the air is pulled past inspiratory valve element 324 into the inspiratory tube 413.

Based on the foregoing, it should now be evident that as a user continues to alternately expire and inspire air via the mask 106, he will inspire air having a lower oxygen concentration than the ambient air. The difference in oxygen concentration between the ambient air and the air inspired via inspiratory tube 102 will be determined by the position of proportioning valve element 448 which determines the amount of ambient air mixed with previously expired air to supply the air for inspiration. The inspired air will be substantially free of any $CO_2$ which is removed by the $CO_2$ absorber cannisters. As is well known in the art, $CO_2$ absorber material typically utilized in anesthesia apparatus exhibits a color change as its ability to absorb further $CO_2$ diminishes. In accordance with the preferred design of the present invention, the cylindrical outer wall 272 of the cannisters 150 and 152 is made transparent so that the user can observe the color of the $CO_2$ absorber material 268 through the vertical spaces separating the columnar members 120, 121, 122 and 123. When the $CO_2$ absorber material 268 has changed color sufficiently, the $CO_2$ absorber cannisters 150 and 152 can easily be replaced by disassembling the assembly 100 by unthreading the knurled nut 166.

From the foregoing, it should now be recognized that a breathing method and apparatus has been disclosed herein for enabling a user at a certain altitude to breathe air having a reduced oxygen concentration in order to simulate a higher altitude. Oxygen-reduced air for inspiration is provided by mixing a selected amount of ambient air with previously expired and stored air. Although a preferred embodiment of the invention has been specifically disclosed herein, variations and alternative embodiments will, of course, readily occur to those skilled in the art which fall within the scope of the invention claimed herein.

For example only, although a particular preferred structural arrangement has been disclosed for storing a quantity of expired air, it is recognized that other container structures can be employed. Thus, attention is briefly directed to FIG. 10 which illustrates a further exemplary structural arrangement of the present invention in which a length of open conventional corrugated tubing 478 is employed to store air expired by the user. The embodiment of FIG. 10 utilizes a housing 480 defining first and second $CO_2$ absorber material compartments 482 and 484 separated by a wall 486 spaced slightly from the floor 488 of housing 480. Ports 490 and 492 respectively open into compartments 482 and 484. Inspiratory tube 494 is coupled to port 490. Expiratory tube 496 is coupled through a valve mechanism 498 comprised of spaced expiratory and inspiratory valves 500 and 502, to port 492. The storage tube 478 opens into the valve mechanism between the spaced valves 500 and 502 and opens to the environment at its remote end. On expiration, expired air flows from mask 504 through expiratory tube 496 and into storage tube 478. On inspiration, air is drawn from the storage tube 478, past the inspiratory valve 502, through the $CO_2$ absorber material in compartment 482, around the wall 486, through the $CO_2$ absorber material in compartment 484, and thence through port 490 to the inspiratory tube 494.

In the simple embodiment illustrated in FIG. 10, the storage tube 478 should have a capacity no greater than about 70% of the tidal volume of the user such that on expiration, a portion (e.g. $\leqq 30\%$) of the expired gas will be lost to the environment and on inspiration an equal amount of ambient air will be drawn from the environment. Thus, for a given user breathing with constant tidal volume (e.g. at rest), the length of the storage tube will determine the altitude simulated. Thus, the user can simulate a higher altitude merely by employing a longer storage tube 478.

Although an embodiment of the invention, as illustrated in FIG. 10, will function to supply air having a reduced oxygen concentration to the user, the length of the air storage tube 478 required to simulate a particular altitude must be custom sized to the particular user. As an alternative to using different length storage tubes, a single storage tube having ports formed therein along the length thereof can be provided (not shown). All of the ports can be closed except one, which thereby effectively establishes the length of the tube and thereby establishes the amount of expired air which will be rebreathed and thus the altitude simulated.

As a still further alternative (not shown), a proportioning valve open to the environment, similar to valve 40 (FIG. 2), can be incorporated in the valve mechanism 498 of FIG. 10 so as to enable different altitudes to be simulated while using only a single fixed length storage tube. Such an embodiment would function in the same manner as described in connection with FIG. 1 except that the open tube would store the expired air in lieu of the storage container 32 of FIG. 1. In still further arrangements of the invention (not shown), other types of air storage chambers can be employed, such as conventional breathing bags normally used in anesthesia delivery systems.

Thus, it should now be apparent that an apparatus has been disclosed useful for conveniently conditioning users to high altitudes. The apparatus is inherently safe because any leak in the system merely causes the user to inspire a greater proportion of ambient air. Moreover, it is preferable to use either a nose or mouth mask, rather than a full face mask, so in the event the user becomes unconscious, he will naturally breathe through the other path and thereby inspire ambient air. It should further be recognized that use of the apparatus in accordance with the invention does not increase $PCO_2$ or decrease Ph in the body, as does heavy exercise. Thus, the incidence of cardiac arrhythmas will be considerably less than conditioning by heavy exercise. It should further be noted that embodiments of the invention can be made sufficiently compact and light so as to permit use while doing moderate exercise, such as jogging.

I claim:

1. Apparatus for supplying air for inspiration by a user having a lower oxygen concentration than the ambient air, said apparatus comprising:
    inspiratory path means having open first and second ends and including means therein for permitting air flow only in the direction from said second to said first end;
    expiratory path means having open first and second ends and including means therein for permitting air flow only in the direction from said first to said second end;
    air reservoir means;
    means coupling said expiratory path means second end to said reservoir means for supplying air thereto; and
    means coupling said inspiratory path means second end to said ambient air and said reservoir means for drawing air therefrom to supply a selected ratio of ambient air and air from said reservoir means to said inspiratory path means first end; and means for removing $CO_2$ from air flowing between said expiratory path means first end and said inspiratory path means first end.

2. The apparatus of claim 1 wherein said means coupling said inspiratory path means second end includes means for establishing the ratio between air drawn from said ambient air and from said reservoir means.

3. Apparatus for supplying air for inspiration by a user having a lower oxygen concentration than the ambient air, said apparatus comprising:
    inspiratory path means having open first and second ends and including means therein for permitting air flow only in the direction from said second to said first end;
    expiratory path means having open first and second ends and including means therein for permitting air flow only in the direction from said first to said second end;
    reservoir means having an entrance opening; and
    air mixing means defining first and second ports respectively communicating with said ambient air and said reservoir means entrance opening and a third port communicating with said inspiratory path second end and said expiratory path second end whereby a selected ratio of ambient air and air from said reservoir means is supplied to said inspiratory path means first end; and
    means in said inspiratory path means for absorbing $CO_2$.

4. The apparatus of claim 3 wherein said air mixing means includes adjustable valve means for varying the ratio of air flowing through said first and second ports.

5. The apparatus of claim 3 further including air passage means for coupling said inspiratory path means first encd and said expiratory path means first end to a user's airway.

6. The apparatus of claim 3 wherein said reservoir means includes substantially rigid walls defining a certain interior storage volume.

7. Apparatus useful in combination with first and second breathing tubes having first ends coupled to a mask adapted to communicate with a user's airway for supplying air to said mask having a lower oxygen concentration than the ambient air, said apparatus comprising:
    a housing defining a fixed volume air storage chamber having an entrance opening;
    expiratory port means defined in said housing communicating with both said air storage chamber entrance opening and the ambient air for respectively supplying user expired air thereto in accordance with a selected ratio, said expiratory port means adapted to be coupled to the second end of said first tube;
    $CO_2$ absorber means for permitting air flow between first and second openings thereof;
    means for communicating said air storage chamber entrance opening with said absorber means first opening; and inspiratory port means defined in said housing communicating with said absorber means second opening for drawing air comprised of air from said storage chamber and ambient air substantially in accordance with said selected ratio, said inspiratory port means adapted to be coupled to the second end of said second tube.

8. The apparatus of claim 7 wherein said expiratory port means includes expiratory valve means for permitting air flow in one direction only from said first tube to said air storage chamber entrance opening in response to a positive pressure in said first tube.

9. The apparatus of claim 8 wherein said inspiratory port means includes inspiratory valve means for permitting air flow in one direction only from said absorber means second opening to said second tube in response to a negative pressure in said second tube; and further including:
mixing chamber means open to said ambient air and located (1) between said expiratory valve means and said air storage chamber entrance opening for supplying air thereto in response to a positive pressure in said first tube and (2) between said air storage chamber entrance opening and said absorber means first opening for supplying air thereto in response to a negative pressure in said second tube.

10. The apparatus of claim 9 including proportioning valve means for adjusting the flow between said mixing chamber and said ambient air.

11. The apparatus of claim 7 wherein said inspiratory port means includes inspiratory valve means for permitting air flow in one direction only from said absorber means second opening to said second tube in response to a negative pressure in said second tube.

12. The apparatus of claim 7 wherein said air storage chamber is defined by an elongated air flow path extending from said entrance opening to a remote end; and
means opening said air flow path to said ambient air proximate to said remote end.

13. Apparatus useful in combination with first and second breathing tubes having first ends coupled to a mask adapted to communicate with a user's airway for supplying air to said mask having a lower oxygen concentration than the ambient air, said apparatus comprising:
a housing including spaced vertically oriented inner and outer walls defining a columnar air storage volume therebetween, said inner wall enveloping a central cavity;
a tube having open first and second ends vertically supported in said cavity;
first air passage means in said housing for communicating said tube second end with a first end of said columnar air storage volume;
said housing defining an air mixing chamber opening to said ambient air and to the first end of said tube;
expiratory port means defined in said housing adapted to be coupled to the second end of said first breathing tube for supplying user expired air to said air mixing chamber in response to a positive pressure in said breathing tubes;
cannister means including spaced first and second perforated plates horizontally disposed in said cavity for retaining $CO_2$ absorber material therebetween;
second air passage means in said housing for communicating said air mixing chamber with said cannister means first perforated plate; and inspiratory port means defined in said housing adapted to be coupled to the second end of said second breathing tube for drawing air from said cannister means second perforated plate in response to a negative pressure in said breathing tubes.

14. The apparatus of claim 13 including proportioning valve means for adjusting the flow between said mixing chamber and said ambient air.

15. The apparatus of claim 13 wherein the end of said columnar air storage volume remote from said first end is open to said ambient air.

16. The apparatus of claim 13 wherein said cannister means comprises a toroidal housing including said first and second perforated plates and concentric spaced inner and outer walls;
means supporting said cannister means in said housing central cavity around said tube with said cannister means inner wall spaced from said tube to define said second air passage means therebetween.

17. The apparatus of claim 16 wherein said cannister means outer wall is formed of transparent material; and wherein
said housing inner and outer walls includes slot means formed therein for providing visual access to said cannister means outer wall.

18. Apparatus useful in an ambient air environment for supplying air for inspiration by a user, said apparatus including:
source means for supplying air having a lower oxygen concentration than that of said ambient air, said source means including storage means for storing a quantity of air;
means for combining a quantity of said air of lower oxygen concentration with a quantity of said ambient air in accordance with a selected ratio;
means for supplying said combined air quantities to a user for inspiration;
means for collecting air expired by a user for storage in said storage means; and
means for removing carbon dioxide from said expired air.

19. The apparatus of claim 18 wherein said means for combining includes means for selectively proportioning said quantities of lower oxygen air and ambient air.

20. A method of supplying air for inspiration by a user comprising the steps of:
collecting a quantity of the user's expired air;
combining said quantity of expired air with a quantity of ambient air in a selected ratio;
supplying said combined air to said user; and
removing carbon dioxide from said collected quantity of expired air.

21. The method of claim 20 wherein said step of combining said air quantities includes the further step of selectively proportioning the quantities of air combined.

22. Apparatus for supplying air for inspiration by a user having a lower oxygen concentration than the ambient air, said apparatus comprising:
inspiratory path means having open first and second ends and including means therein for permitting air flow only in the direction from said second to said first end;
expiratory path means having open first and second ends and including means therein for permitting air flow only in the direction from said first to said second end;
reservoir means having an entrance opening; and air mixing means defining first and second ports respectively communicating with said ambient air and said reservoir means entrance opening and a third port communicating with said inspiratory path second end and said expiratory path second end whereby a selected ratio of ambient air and air from said reservoir means is supplied to said inspiratory path means first end;

said reservoir means additonally including an overflow opening; and wherein said reservoir means comprises a housing enclosing a certain volume, said housing including baffle means mounted therein defining a segmented series flow path between said entrance opening and said overflow opening.

* * * * *